United States Patent
Prince et al.

(10) Patent No.: US 10,071,263 B1
(45) Date of Patent: Sep. 11, 2018

(54) PIVOTING MULTILEAF COLLIMATOR AND METHOD FOR LARGE FIELD COVERAGE

(71) Applicant: Varian Medical Systems, Inc., Palo Alto, CA (US)

(72) Inventors: Steven W. Prince, San Francisco, CA (US); Stanley Mansfield, Sunnyvale, CA (US); Stuart Scollay, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1464 days.

(21) Appl. No.: 14/225,413

(22) Filed: Mar. 25, 2014

(51) Int. Cl.
*G21K 1/00* (2006.01)
*A61N 5/00* (2006.01)
*A61N 5/10* (2006.01)

(52) U.S. Cl.
CPC ......... *A61N 5/1047* (2013.01); *A61N 5/1081* (2013.01)

(58) Field of Classification Search
CPC ....... G21K 1/046; G21K 1/043; A61N 5/1045
See application file for complete search history.

(56) References Cited

U.S. PATENT DOCUMENTS

| | | |
|---|---|---|
| 4,489,426 A | 12/1984 | Grass |
| 4,868,844 A | 9/1989 | Nunan |
| 4,987,309 A | 1/1991 | Klasen |
| 5,591,983 A | 1/1997 | Yao |
| 6,144,875 A | 11/2000 | Schweikard |
| 6,266,393 B1 | 7/2001 | Ein-Gal |
| 6,526,123 B2 | 2/2003 | Ein-Gal |
| 6,600,810 B1 | 7/2003 | Hughes |
| 6,977,987 B2 | 12/2005 | Yamashita |
| 7,085,347 B2 | 8/2006 | Mihara |
| 7,095,823 B2 | 8/2006 | Topolnjak |
| 7,188,999 B2 | 3/2007 | Mihara |
| 7,221,733 B1 | 5/2007 | Takai |
| 7,239,684 B2 | 7/2007 | Hara |
| 7,386,099 B1 | 6/2008 | Kasper |
| 8,637,841 B2 | 1/2014 | Prince |
| 9,082,520 B2 | 7/2015 | Prince |
| 9,324,468 B2 | 4/2016 | Mansfield |
| 2001/0043669 A1 | 11/2001 | Ein-Gal |

(Continued)

FOREIGN PATENT DOCUMENTS

| | | |
|---|---|---|
| DE | 19905823 C1 | 6/2000 |
| EP | 0314214 A2 | 5/1989 |

(Continued)

OTHER PUBLICATIONS

Hirai et al. "State-of-the-Art Medical Treatment Machines MHI-TM2000," Mitsubishi Heavy Industries Technical Review, Mar. 2009, vol. 46 No. 1, pp. 29-32.

(Continued)

*Primary Examiner* — Dani Fox
(74) *Attorney, Agent, or Firm* — Houst Consulting

(57) ABSTRACT

A radiation apparatus includes a source operable to generate a radiation beam, a multileaf collimator operable to shape of the radiation beam, and a pivoting mechanism configured to pivot the multileaf collimator about the source. The radiation apparatus may further include a rotating mechanism configured to rotate the multileaf collimator about an axis passing through the source and the multileaf collimator.

25 Claims, 12 Drawing Sheets

(56) References Cited

U.S. PATENT DOCUMENTS

| | | |
|---|---|---|
| 2002/0101959 A1 | 8/2002 | Kato |
| 2004/0079899 A1 | 4/2004 | Ma |
| 2004/0168536 A1 | 9/2004 | Bellouard |
| 2004/0184578 A1 | 9/2004 | Nakano |
| 2005/0008123 A1 | 1/2005 | Topolnjak |
| 2006/0193441 A1 | 8/2006 | Cadman |
| 2007/0176126 A1 | 8/2007 | Hashimoto |
| 2009/0041200 A1 | 2/2009 | Lu |
| 2009/0207975 A1 | 8/2009 | Bourne |
| 2010/0189220 A1 | 7/2010 | Flynn |
| 2010/0252754 A1 | 10/2010 | Brown |
| 2012/0043481 A1* | 2/2012 | Mansfield ............ A61N 5/1045 250/492.1 |
| 2014/0112453 A1 | 4/2014 | Prince et al. |
| 2015/0273239 A1 | 10/2015 | Hsu |

FOREIGN PATENT DOCUMENTS

| | | |
|---|---|---|
| EP | 0562644 A1 | 9/1993 |
| JP | 03009767 | 1/1991 |
| JP | 07-067491 B2 | 7/1995 |
| JP | H07255716 A | 10/1995 |
| WO | 2008/076035 A1 | 6/2008 |
| WO | 2009056151 A1 | 5/2009 |

OTHER PUBLICATIONS

PCT, International Search Report and Written Opinion in International Application No. PCT/US2011/048201, dated Mar. 19, 2012, 12 pages.

PCT, International Search Report and Written Opinion in International Application No. PCT/US2011/048203, dated Mar. 23, 2012, 9 pages.

EPO, Extended European Search Report in European Application No. 11820404.9, dated Feb. 5, 2015, 5 pages.

State Intellectual Property Office of China, Search Report and Office Action in Chinese Application No. 201180042834.3, dated Mar. 25, 2015, 13 pages.

* cited by examiner

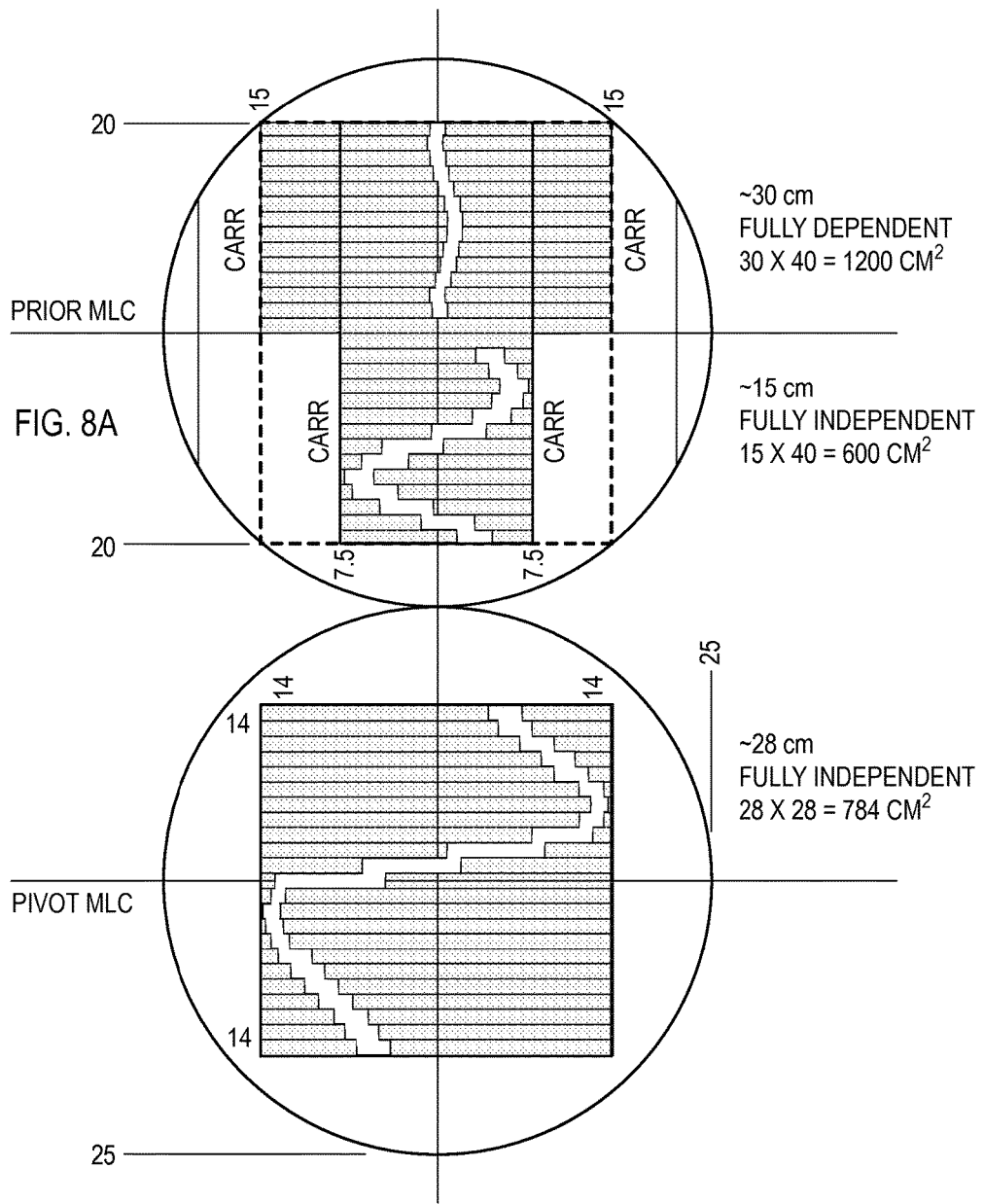

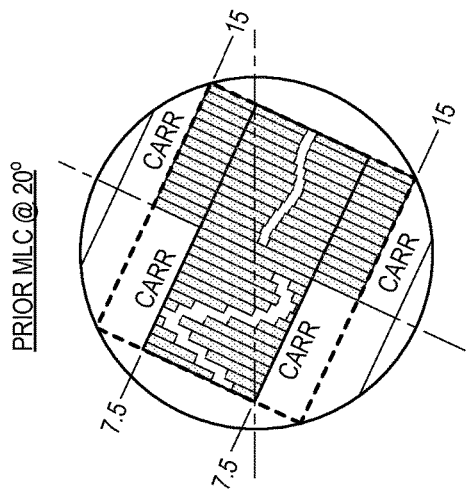
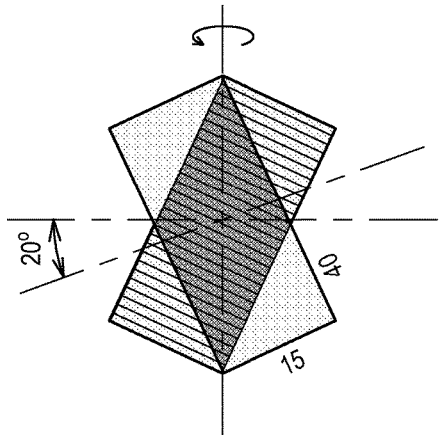
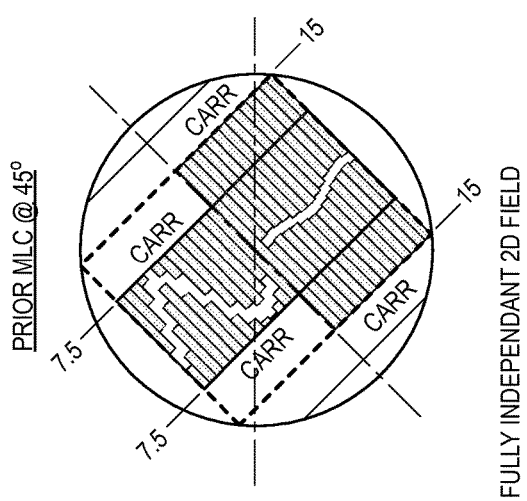
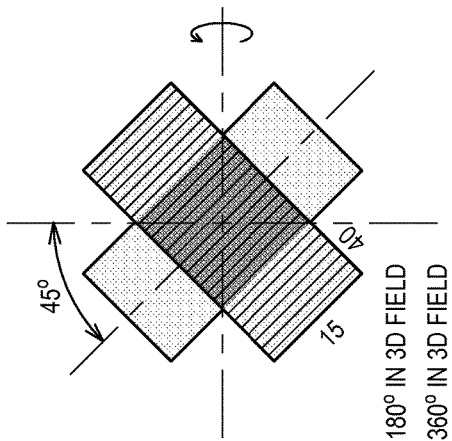
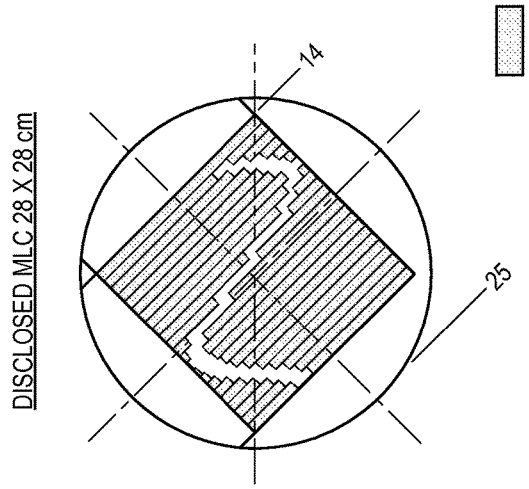
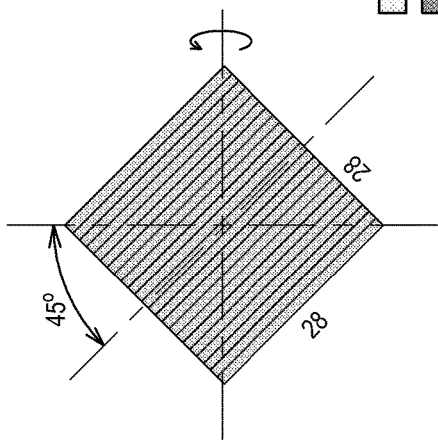
FIG. 9A  FIG. 9B  FIG. 9C

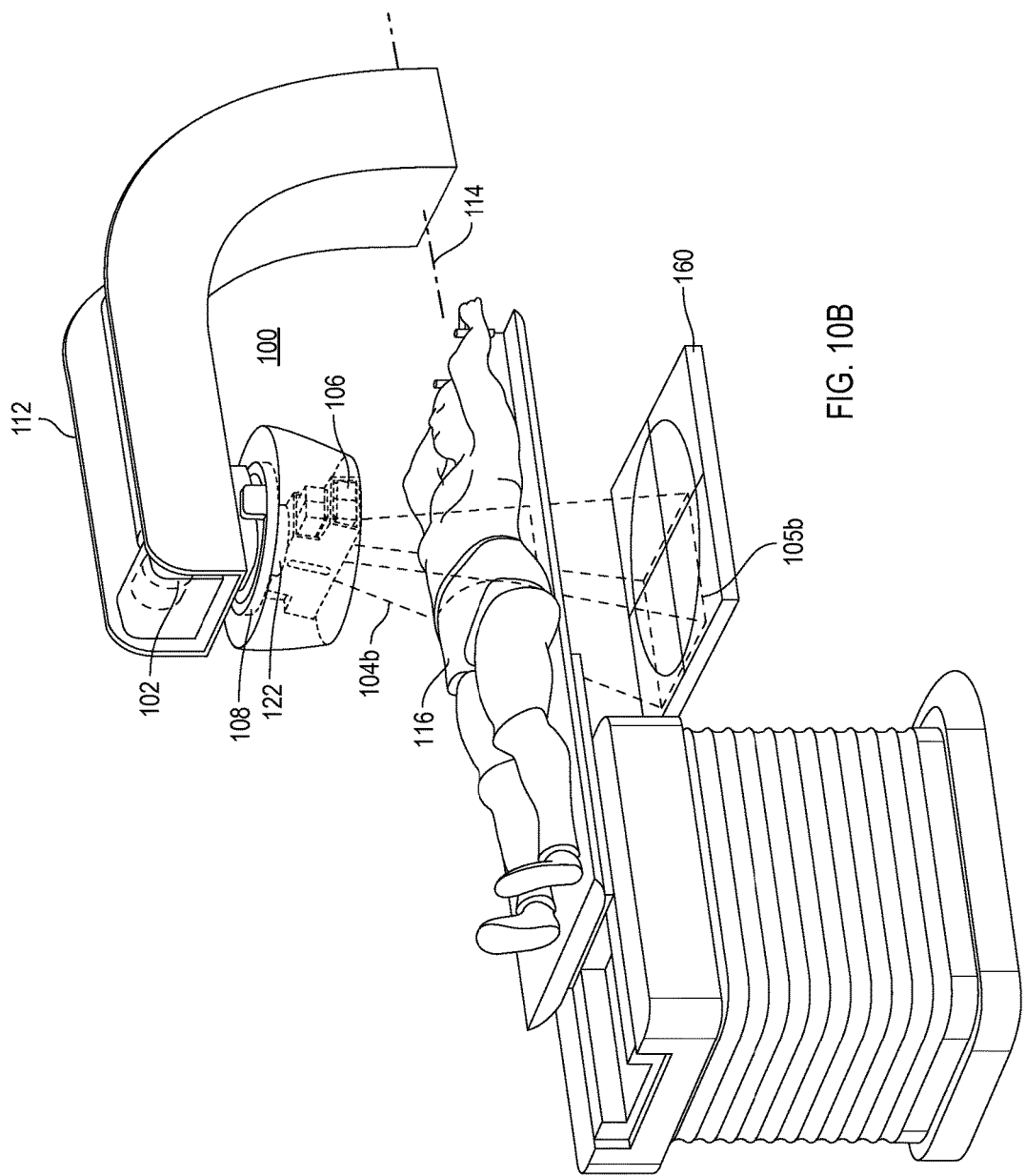

PIVOTING MULTILEAF COLLIMATOR AND METHOD FOR LARGE FIELD COVERAGE

TECHNICAL FIELD

Embodiments of this disclosure relate to radiation apparatuses and methods. In particular, multileaf collimators (MLCs) and methods for large field coverage are described.

BACKGROUND

Conventional MLCs have generally been designed with the ability to shape the maximal radiation filed size that a medical linear accelerator (MLA) can produce in one instantaneous static exposure. Maximal field size is typically 40×40 cm$^2$ in the patient plane produced by a radiation source 100 cm distant. However, conventional MLCs face a design dilemma in that the MLC leaf tips cannot be extended far from their carriage boxes. A relatively large cantilevered extension may increase the variance in the leaf tip lateral position, thus increasing leaf gap leakage and possibility of colliding with adjacent leaves.

To solve this dilemma, some conventional MLCs make leaf tails very long so that the leaf tips can be cantilevered with more precision from a non-moving (carriageless) leaf box. This leads to expensive heavy leaves and bulky, large collimators. Field shaping flexibility is limited by the leaf tip over-travel beyond the centerline. However, the leaf overtravel is generally not enough to block the entire filed. Some conventional MLCs put shorter leaves in a moving carriage box on reach side. Leaf cost and cover diameter are more acceptable but field shaping flexibility depend on the instantaneous leaf reach, or the projected distance between the most extended and the most retracted leaf tip on the same carriage box.

Dynamic treatment techniques such as intensity modulated radiotherapy (IMRT) and volumetric modulated arc therapy (VMAT) are rapidly being adopted in radiation treatment. These techniques change the paradigm of MLC use from Cerrobend block replacement to that of achieving complex 2D or 3D dose distribution goals. IMRT techniques produce good dose distributions from superposition of several dynamic ports. IMRT works well with carriage MLCs since the sliding window can be synchronized to not require large leaf reach. VMAT techniques are also successful for good dose distribution, especially for short treatment times. However, VMAT techniques are inherently limited by MLCs which have not been designed with such complex techniques in mind. Leaf reach and carriage position limitations have not suited VMAT optimally. For instance, in a conventional MLC, the instantaneously available fully independent field shaping area is only 15×40 cm$^2$ because the leaf reach is only 15 cm. Independent field shaping area of 30×40 cm$^2$ is theoretically available, but the dependencies of leaf travel range on leaf reach and carriage position limit instantaneous shaping ability so significantly that only slightly more than 15×40 cm$^2$ is typically practical.

Accordingly, there is a need for MLCs that can overcome the problems associated with conventional MLCs. There is a need for MLCs that can cover most clinical treatments as well as or better than conventional MLCs but by using fewer leaves for less cost and higher reliability.

SUMMARY

Conventional MLC development trends have been to increase both field size and resolution. This requires a large number of leaves, increasing cost and decreasing reliability of MLCs. For example, a conventional MLC may require 160 leaves to provide a 5 mm resolution or as many as 320 leaves for a 2.5 mm resolution.

Embodiments of this disclosure are conceived to curb this trend by providing only enough leaves to cover common field sizes and by facilitating special techniques of nearly equal effectiveness for larger field sizes. For example, common sizes less than e.g. 28×28 cm$^2$ can be covered with single exposures while larger field sizes may be covered with multiple exposures using the techniques described in this disclosure.

Conventional MLCs have significant and complex limitations and tradeoffs in VMAT. Conventional carriageless MLCs can only effectively shape volumes within their leaf retract and overtravel limits. Carriage MLCs generally do not move the carriage during one arc of VMAT treatment and they can only effectively shape volumes within the single leaf reach.

Embodiments of this disclosure overcome the prior art limitations by using a carriageless MLC that can provide full overtravel. Leaf reach may equal the field size so that each pair of leaf tip positions in a treatment planning strip is fully independent of all of the other pairs of leaf tip positions in the other treatment planning strips. With a smaller instantaneous field size (e.g. 28×28 cm$^2$), embodiments of this disclosure can provide for both a larger, fully independent area for IMRT treatments and larger, fully independent volume for VMAT treatment compared to most conventional MLCs.

Embodiments of this disclosure allow the MLC to pivot about the radiation source in various degrees of freedom. By way of example, a pivoting MLC with a two-degree of freedom in pivoting allows for easy matching of e.g. 28×28 cm$^2$ exposures, in either longitudinal, lateral or any direction in the patient plane, simply by pivoting the MLC such that the bounding planes shared by two or more exposures are coincident. The easy field combining using an MLC with a two-degree of freedom pivoting would be then limited only by the circular field size set by the fixed primary collimator in the linear accelerator, which is typically a e.g. 50 cm circle. Two exposures can cover a 50×28 cm$^2$ field. A quadrant of four pivot exposures can cover the entire 50 cm circle.

In conventional treatment planning for field matching, dynamic motion of jaws or MLC leaves are used to "blur" the sharp field edges. This "seaming" may reduce the under or over dose effect in case of position errors. Embodiments of this disclosure allow the use of treatment planning algorithms and dynamic motion to make this seaming automatic and substantially invisible to the user when choosing a field larger than e.g. 28×28 cm$^2$ that requires multiple exposures. Seaming can be performed both for bounding planes in the leaf travel direction and for bounding planes perpendicular to the leaf travel direction.

Conventional MLCs cannot perform an isocentric VMAT treatment wider than 40 cm. Embodiments of this disclosure with one- or two-degree of freedom of pivoting allow for combination of extra e.g. two half-fan VMAT arcs.

This Summary is provided to introduce selected embodiments in a simplified form and is not intended to identify key features or essential characteristics of the claimed subject matter, nor is it intended to be used as an aid in determining the scope of the claimed subject matter. Other embodiments of the disclosure are further described in the Detail Description.

BRIEF DESCRIPTION OF THE DRAWINGS

These and other features and advantages of the disclosed methods and apparatuses will become better understood upon reading of the following detailed description in conjunction with the accompanying drawings and the appended claims provided below, where:

FIG. 8A illustrates independent 2D field shaping using a conventional multileaf collimator;

FIG. 8B illustrates independent 2D field shaping using a multileaf collimator according to some embodiments of this disclosure;

FIG. 9A illustrates independent 3D field shaping using a multileaf collimator according to some embodiments of this disclosure;

FIGS. 9B and 9C illustrate independent 3D field shaping using a conventional multileaf collimator;

FIGS. 10A and 10B illustrate a radiation method according to some embodiments of this disclosure.

DETAILED DESCRIPTION

Figure 1:
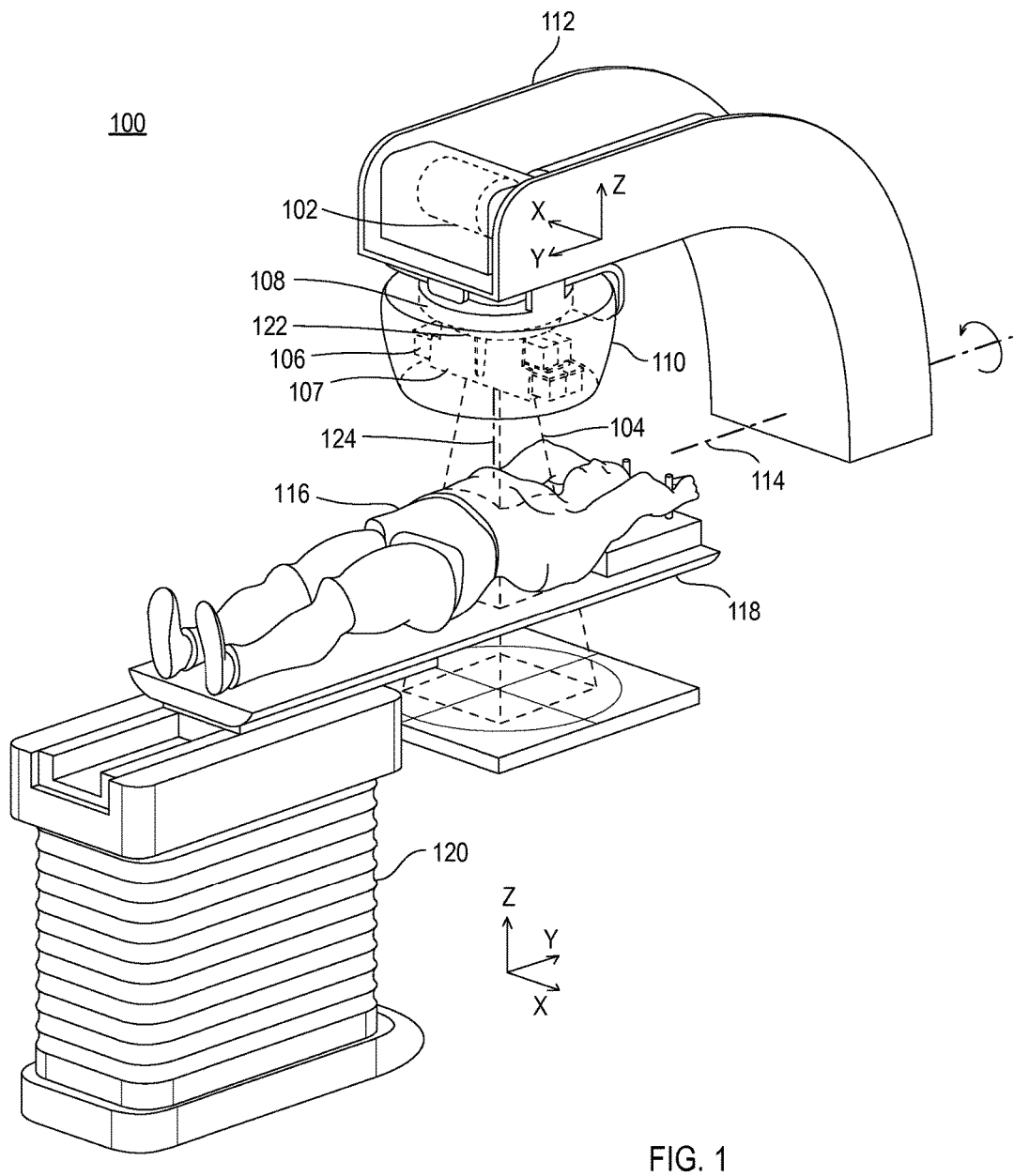
FIG. 1 is a schematic illustration of a radiation apparatus according to some embodiments of this disclosure.

Various embodiments of multileaf collimators and methods are described. It is to be understood that the disclosure is not limited to the particular embodiments described as such may, of course, vary. An aspect described in conjunction with a particular embodiment is not necessarily limited to that embodiment and can be practiced in any other embodiments. Further, in the following description, numerous specific details such as examples of specific components, dimensions, processes, etc. may be set forth in order to provide a thorough understanding of the disclosure. It will be apparent, however, to one of ordinary skill in the art that these specific details need not be employed to practice embodiments of the disclosure. In other instances, well known components or steps may not be described in detail in order to avoid unnecessarily obscuring the embodiments of the disclosure.

Various relative terms such as "above," "below," "top," "bottom," "forward," and "backward," etc. may be used to facilitate description of various embodiments. The relative terms are defined with respect to a conventional orientation of a structure and do not necessarily represent an actual orientation of the structure in manufacture or use. The following detailed description is, therefore, not to be taken in a limiting sense. As used in the description and appended claims, the singular forms of "a," "an," and "the" may include plural references unless the context clearly dictates otherwise.

As used herein, the term "multileaf collimator" or MLC refers to a device that includes a plurality of beam blocking leaves each of which can be independently moved in and out of a beam to modify one or more parameters of the beam such as the beam shape, size, energy, or intensity etc. The beam blocking leaves are generally arranged in pairs and disposed in opposing banks. The beam blocking leaves of each pair may be longitudinally movable relative to each other.

As used herein, the term "carriage MLC" refers to a multileaf collimator which is supported by one or more movable carriages. The one or more movable carriages may be translated in a linear direction in addition to the individual leaf travel. A carriage MLC may include a single movable carriage (unicarriage) carrying all the beam blocking leaves. A carriage MLC may also include two carriages each carries a bank of beam blocking leaves. The two carriages may be separately movable relative to each other.

As used herein, the term "carriageless MLC" refer to a multileaf collimator which does not include a movable carriage.

As used herein, the term "subject" refers to a human, animal, and any object of interest that can be irradiated by the apparatuses and methods described herein.

In some aspect, a radiation apparatus is provided. The apparatus includes a source operable to generate a radiation beam, a multileaf collimator operable to shape the radiation beam, and a pivoting mechanism configured to pivot the multileaf collimator about the source.

In some embodiments, the radiation apparatus may further include a rotating mechanism configured to rotate the multileaf collimator about the source. The rotating mechanism may be supported by and pivotable with the pivoting mechanism. Alternatively, the pivoting mechanism may be supported by and rotatable with the rotating mechanism.

The multileaf collimator may be a carriage MLC. Alternatively, the multileaf collimator may be a carriageless MLC.

In conjunction with any of the embodiments described in this disclosure, the pivoting mechanism may include a first pivoting mechanism configured to pivot the multileaf collimator about the source with a first degree of freedom and a second pivoting mechanism configured to pivot the multileaf collimator about the source with a second degree of freedom. In some embodiments, the pivoting mechanism may include a universal joint structure configured to pivot the multileaf collimator about the source in all degrees of freedom.

In conjunction with any embodiments described in this disclosure, the plurality of pairs of leaves of the multileaf collimator may be operable to define a maximal aperture when the leaves are fully retracted. The maximal aperture may have a first dimension in a leaf travel direction, and at least some of the leaves have a travel length that is at least equal to the first dimension. In some embodiments, each of the leaves of the multileaf collimator has a travel length that is at least equal to the first dimension.

In an exemplary embodiment, the plurality of leaves of the multileaf collimator may be operable to define a maximal aperture in a shape of a square, defining a maximal treatment field of about 28×28 $cm^2$ in an isocenter plane about 100 cm distant from the source. Each of the plurality of leaves has a travel range that is at least equal to the maximal aperture.

In conjunction with any embodiments described in this disclosure, the plurality of leaves of the multileaf collimator may be arranged in two or more levels with respect to the source. In conjunction with any embodiments described in this disclosure, the multileaf collimator may include leaves with variable leaf widths, for example, thinner leaves in the middle (first) section and wider leaves on either side of the thinner leaves (second section).

In some aspect, a method of delivering radiation using a radiation apparatus is provided. The radiation apparatus may include a source operable to generate a radiation beam and a multileaf collimator operable to shape the radiation beam. In the method, the radiation source is positioned at a location relative to the subject. While the source remains at the location, the multileaf collimator is positioned relative to the source at a first position and a first beam is deliver, wherein the multileaf collimator shapes the first beam to define a first treatment field in a first area in the subject. The multileaf collimator is then pivoted about the source to a second position and a second beam is delivered, wherein the multileaf collimator shapes the second beam to define a second treatment field in a second area in the subject. The first and second treatment fields jointly provide a combined treatment field covering the first and second areas in the subject.

In conjunction with any embodiments described in this disclosure, the plurality of pairs of the multileaf collimator used may be operable to cover a maximal treatment area in the subject when the leaves are fully retracted. The maximal treatment area may have a first dimension in a leaf travel direction, and each of the leaves of the multileaf collimator may have a travel range to fully cover the entire first dimension.

In some embodiments, the maximal treatment area is in a shape of a square, for example, about 28×28 cm$^2$ or greater. In some embodiments, the treatment field defined may have a step resolution of about 5 mm or smaller.

In some embodiments, while the source remains at the location, the multileaf collimator may be pivoted sequentially to a plurality of positions. The multileaf collimator may shape beams at the plurality of portions and provide a combined treatment field in the subject. For example, while the source remains at the location, the multileaf collimator may be pivoted about the source to a first position thereby defining a first treatment field covering a first area in the subject. Then the multileaf collimator may be pivoted about the source to a second position thereby defining a second treatment field covering a second area in the subject. The multileaf collimator may be pivoted about the source to a third position thereby defining a third treatment field covering a third area in the subject. Then the multileaf collimator may be pivoted about the source to a fourth position thereby defining a fourth treatment field covering a fourth area in the subject. The first, second, third, and fourth treatment fields may be joined using a suitable algorithm providing a combined treatment field. The steps of pivoting the multileaf collimator may be carried out sequentially in a clockwise or counterclockwise order and the first, second, third, and fourth treatment fields may adjoin in any other desirable ways.

In some embodiments, the radiation source may be relocated to additional different locations relative to the subject, and while the source remains at the additional different locations, the pivoting steps are repeated to provide a treatment field.

Exemplary embodiments will now be described with reference to the figures. It should be noted that some figures are not necessarily drawn to scale. The figures are only intended to facilitate the description of specific embodiments, and are not intended as an exhaustive description or as a limitation on the scope of the disclosure.

FIG. 1 schematically shows an exemplary radiation apparatus 100 according to some embodiments of the disclosure. The apparatus 100 may include a source 102 operable to generate a beam 104, a multileaf collimator 106 operable to shape or modulate the intensity of the beam 104, and a pivoting mechanism 108 configured to pivot the multileaf collimator 106 about the source 102. The beam 104 generated by the source 102 may be any radiation beams suitable for treatment and/or imaging, including x-ray beams, electron beams, proton beams, or other particle beams. A housing 110 may enclose the multileaf collimator 106 and other devices not shown in FIG. 1. An arm structure 112, which may support the source 102 and the pivoting mechanism 108, may swivel about an axis 114, allowing the source 102 and multileaf collimator 106 to rotate about the patient 116. Alternatively, the source 102, the multileaf collimator 106, and the pivoting mechanism 108 may be enclosed in an annular ring structure (not shown). The annular ring structure may have an opening for admitting at least a part of the patient body. The patient 116 may be supported by a patient support 118, which may extend from a couch 120 in a cantilevered manner to allow beam delivery to the patient 116 from various angles including from below the patient 116. The couch 120 may be moved vertically (z), laterally (x), and/or longitudinally (y) using various motion mechanisms known in the art.

The pivoting mechanism 108 may be configured to allow the multileaf collimator 106 to pivot about the source 102 in one degree of freedom e.g. generally in y direction or in x-direction. A one-degree of freedom pivot may be desirable for a medical linear accelerator in an annular ring configuration since a two-degree of freedom pivot would pivot out of the ring plane, thus requiring wider or complex moving ring covers.

The pivoting mechanism 108 may be configured to allow the multileaf collimator 106 to pivot about the source 102 in two degrees of freedom e.g. in both y and x directions. A two-degree of freedom pivot may be desirable for a medical linear accelerator in a non-ring configuration, such as one schematically shown in FIG. 1 where an arm structure (e.g. C-arm) may provide support and swivel on an axis.

In some embodiments, the pivoting mechanism 108 may include a universal joint structure to allow the multileaf collimator 106 to pivot about the source 102 in all degrees of freedom. For example, in a simple straight-through linear accelerator, the relatively unencumbered space around the radiation source may allow a structure similar to a universal joint in a socket drive set to be disposed. Alternatively, more expensive curved rails or segment bearings may be arranged to accommodate the volume constraints of more bulky bend magnet and beam generation systems, as will be described in more detail below.

The radiation apparatus 100 may include a rotating mechanism 122 in conjunction with any pivoting mechanism described in this disclosure. Therefore, in addition to pivoting about the source 102, the multileaf collimator 106 may be further rotated about an axis 124 through the source 102 and the collimator 106. The rotating mechanism 122 may be supported by and pivotable with the pivoting mechanism 108. Alternatively, a rotating mechanism may support a pivoting mechanism and rotate the pivoting mechanism along with the multileaf collimator, as will be described in more detail below in conjunction with other exemplary embodiments.

Figure 5:
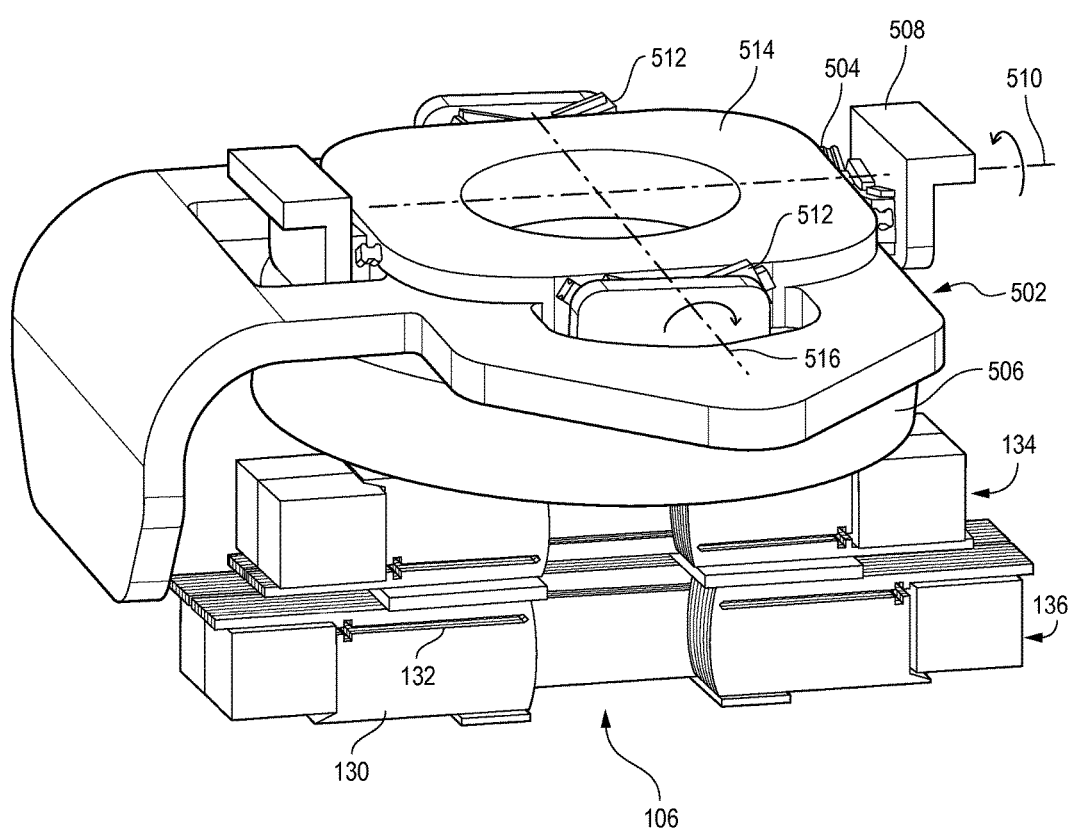
FIG. 5 illustrates an exemplary multileaf collimator coupled to a pivoting mechanism according to some embodiments of this disclosure.

Referring to FIG. 1 and FIG. 5, the multileaf collimator 106 may be supported by a supporting structure 107. The multileaf collimator 106 may include a plurality of beam blocking leaves 130, each of which may be independently moved e.g. in the x-direction by a drive mechanism 132 (FIG. 5). The plurality of beam blocking leaves 130 may be arranged in two banks, forming a plurality of leaf pairs. The beam blocking leaves 130 may be arranged in one level. Alternatively, the beam blocking leaves 130 may be arranged in two or more levels as shown in FIG. 5, forming a proximal (or first) level 134 and a distal (or second) level 136 relative to the source 102. The two or more level configuration may improve the leakage effects and definition of the collimator 106. Each drive mechanism 132 may include a drive motor coupled to a computer and motion control. In operation, the drive motors may receive signals from the computer and motion control and move to position individual leaves 130 relative to the beam 104. The positioning of a leaf operates to block or adjust the radiation beam 104 passing through the volume occupied by the leaf. The combined positioning of all leaves at any time in the execution of a treatment plan may define one or more apertures through which the unblocked radiation beam passes, and the aperture(s) may define the shape of the radiation beam, and thus the shape of the treatment field in the patient. The combined effect of the blocking and open apertures, in conjunction with the pivoting and/or rotating of the multileaf collimator 106, may create a desired three-dimensional radiation dose distribution within the patient.

The individual leaves 130 may be in various configurations in cross section such as rectangle or trapezoid etc. For example, the leaves 130 may have a cross section that is approximately trapezoidal in shape with leaf sides substantially focused on the source. The leaf sides may have smaller features not shown such as steps, waves, or slight tilt to reduce the radiation passing through leaf gaps. The size of the cross sections of the leaves may be same or variable. For example, the multileaf collimator 106 may include a plurality of narrower leaves in the middle section (first section) for providing a higher leaf definition and a plurality of wider leaves on either side of the narrow leaves (second section) for shaping an outer area where a high definition may not be required.

Referring to FIG. 1, the support body 107 of the plurality of beam blocking leaves 130 may include a frame, a box or a carriage etc. In some embodiments, the support body 107 may include a movable carriage, which may be translated in a linear direction e.g. moving in the same direction as the leaf travel direction. In some embodiments, each bank of the beam blocking leaves may be supported by a separate movable carriage, and each carriage may be independently translated in a linear direction, e.g. moving in the same direction as the leaf travel direction. In some embodiments, the movable carriages may optionally tungsten jaws. The use of one or more movable carriages may be advantageous in that individual leaves and their travel can be shorter, and therefore have better tolerance control, less cost, less weight, and can fit within a smaller cover or similar structures. Combined speed of leaves and carriages can be a treatment planning advantage. In some embodiments, the multileaf collimator 106 does not require a movable carriage (carriageless MLC).

Still referring to FIG. 1, in some embodiments, the multileaf collimator 106 may be a carriageless MLC that allows the beam blocking leaves 130 full overtravel. The leaf reach or travel range may equal to the maximal aperture size of the multileaf collimator 106, or each leaf in a bank may be fully extended to the opposing bank when the corresponding opposing leaf is fully retracted. As such, each pair of leaf tip positions in a treatment planning strip can be fully independent of all of the other pairs of leaf tip positions in the other treatment planning strips as will be described in greater detail below. The instantaneous field size provided by the multileaf collimator 106 may be smaller than that provided by some MLCs that do not allow for leaf full overtravel. However, the multileaf collimator 106 with the capability of leaf full overtravel can provide a larger fully independent area for intensity modulated radiotherapy (IMRT) and a larger fully independent volume for volumetric modulated arc therapy (VMAT), as will be described in more detail below.

For illustrative purpose, an exemplary carriageless multileaf collimator of this disclosure may include 112-114 leaves each leaf can fully travel the maximal aperture of the MLC. The leaves may be arranged in two levels, each leaf in a level may offset a leaf in the other level in about a half leaf width. The multileaf collimator may provide a maximal field size of about 28×28 $cm^2$ in the isocenter plane produced by a radiation source located about 100 cm distant from the isocenter. The exemplary multileaf collimator may provide for a step resolution of about 5 mm in shaping the treatment field. In a further exemplary embodiment, a carriageless multileaf collimator may include 224-226 leaves, which may provide for a maximal field size of about 28×28 $cm^2$ with a step resolution of about 2.5 mm in shaping the treatment field. In an additional specific example, a carriageless multileaf collimator may include 98 leaves, which may provide for a maximal field size of about 22×22 $cm^2$ with a step resolution of about 2.5 mm over the middle 8 $cm^2$ in shaping the field and a step resolution of about 5 mm on either side. It should be noted that the details of specific dimensions are provided for illustration and understanding of the disclosure. These specific details are not required to practice embodiments of the disclosure.

Figure 2:
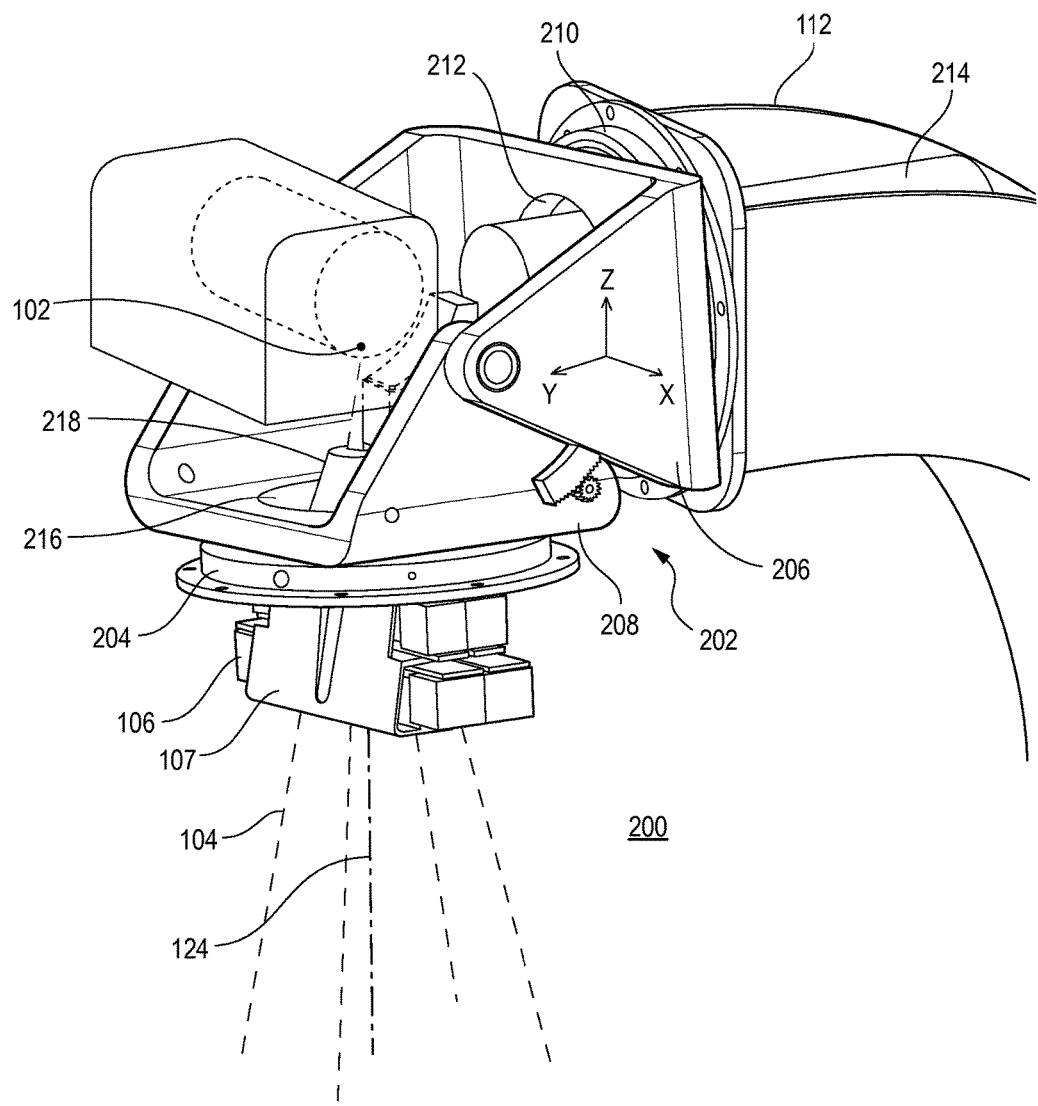
FIG. 2 is a schematic illustration of a portion of a radiation apparatus with exemplary pivoting and rotating mechanisms shown in detail according to some embodiments of this disclosure.

FIG. 2 schematically shows a partial, exemplary radiation apparatus 200. The radiation apparatus 200 may include a source 102, a multileaf collimator 106, a pivoting mechanism 202 configured to pivot the multileaf collimator 106 about the source 102, and a rotating mechanism 204 configured to rotate the collimator 106 about an axis 124 through the source 102 and the collimator 106. The multileaf collimator 106 may be supported by a support structure 107, which may be a movable carriage, or a carriageless structure.

The pivoting mechanism 202 may include a first pivoting member 206 that can rotate on y-axis and a second pivoting member 208 that can rotate on x-axis. The first pivoting member 206 may be coupled to and supported by the arm 112. The second pivoting member 208 may be coupled to and supported by the first pivoting member 206. The rotating member 204 may be coupled to and supported by the second pivoting member 208.

The first pivoting member 206 may include an angle bracket coupled to and supported by the arm 112 via a bearing structure 210. An opening 212 in the angle bracket may allow an accelerator 214 and other devices including a supporting structure for the source 102 to extend through. The second pivoting member 208 may also include an angle bracket coupled to and supported by the first angle bracket via a joint or the like. The second angle bracket may have an opening 216 to allow a fixed collimator 218 placed adjacent to the source 102. The rotating member 204 may include a bearing structure which may couple the multileaf collimator 106 to the second pivoting member 208. The angle brackets of the first and second pivoting members 206, 208 may advantageously provide space for the source 102 and other devices and clearance preventing collision between the pivoting members and sources and other devices.

In operation, a rotation of the first pivoting member 206 on y-axis may cause the second pivoting member 208, the rotating member 204, and the multileaf collimator 106 to pivot about the source 102 generally in x-direction. A rotation of the second pivoting member 208 on x-axis may cause the rotating member 204 and the multileaf collimator 106 to pivot about the source 102 generally in y-direction. A rotation of the rotating member 204 may cause the multileaf multileaf 106 to rotate about an axis 124 through the source 102 and the multileaf collimator 106. By way of example, the first pivoting member 206 may rotate on y-axis both clockwise and counterclockwise. The second pivoting member 208 may rotate on x-axis both forward and backward. The rotating member may rotate on axis 124 both clockwise and counterclockwise. It will be appreciated by one of ordinary skill in the art that the rotation degrees of the pivoting and rotating mechanisms can be modified depending on specific applications and this disclosure is not limited to the specific examples.

Figure 3:
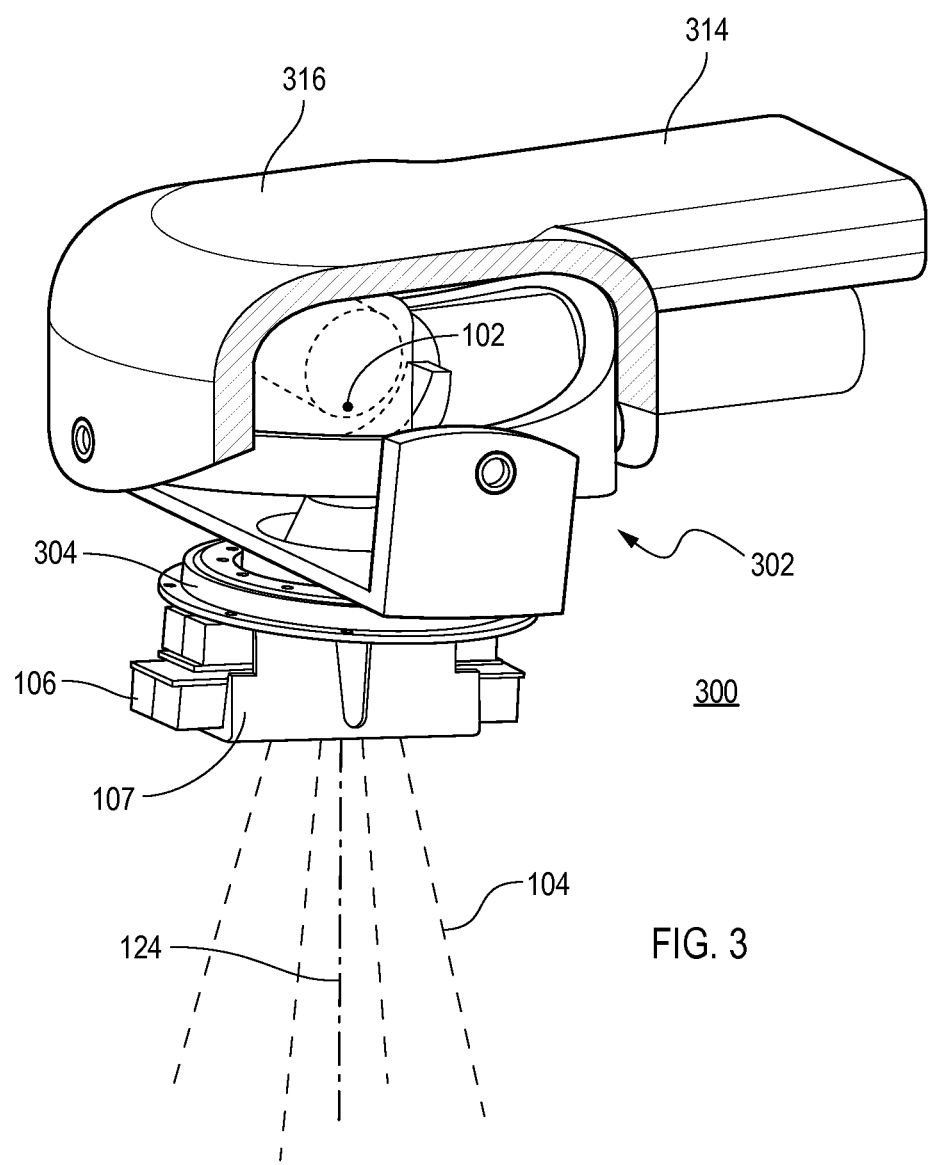
FIG. 3 is a schematic illustration of a portion of a radiation apparatus with exemplary pivoting and rotating mechanisms shown in detail according to some other embodiments of this disclosure.
Figure 4:
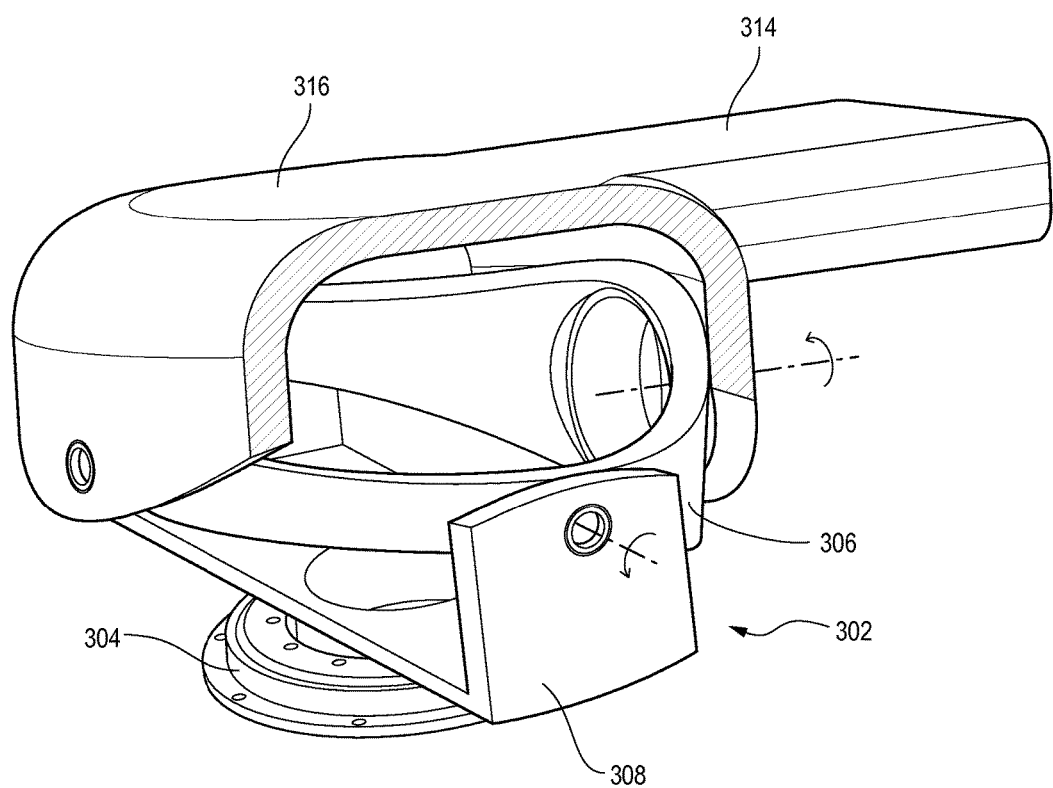
FIG. 4 illustrates exemplary pivoting and rotating mechanisms in detail according to some embodiments of this disclosure.

FIG. 3 schematically shows a partial, exemplary apparatus 300, which includes a source 102, a multileaf collimator 106, which may be supported by a supporting structure 107, a pivoting mechanism 302 configured to pivot the multileaf collimator 106 about the source 102, and a rotating mechanism 304 configured to rotate the multileaf collimator 106 about an axis 124 through the source 102 and the multileaf collimator 106. In comparison, the apparatus 300 shown in FIG. 3 may be similar to the apparatus 200 shown in FIG. 2 in many aspects. Unlike the apparatus 200 shown in FIG. 2, the pivoting mechanism 302 of the apparatus 300 shown in FIG. 3 may include a universal joint structure. FIG. 4 schematically shows the universal joint structure 302 in greater detail. A first stage 306 may be coupled to an arm structure 314 and provide a first degree of freedom pivot. A second stage 308 may be coupled to the first stage 306 and provide a second degree of freedom pivot. With the universal join structure 302 shown in FIGS. 3-4, some devices including band magnets etc. may be mounted to the helmet structure 316 of the arm 314.

FIG. 5 schematically shows another exemplary universal joint structure 502 including segment rails constructed to facilitate pivoting the multileaf collimator 106 about the source. A first pair of segment rails 504 may couple a first stage 514 to a mounting structure 508, which in turn may be fixedly mounted to a gantry or arm structure. Actuation of the first pair of segment rails 504 may allow the first stage 514 to pivot on the first pivot axis 510, causing the multileaf collimator 106 to pivot about the source in a first degree of freedom. A second pair of segment rails 512 may couple a second stage 506 to the first stage 514. Actuation of the second pair of segment 512 rails may allow the second stage 506 to pivot on the second pivot axis 516, causing the multileaf collimator 106 to pivot about the source in a second degree of freedom.

Figure 6:
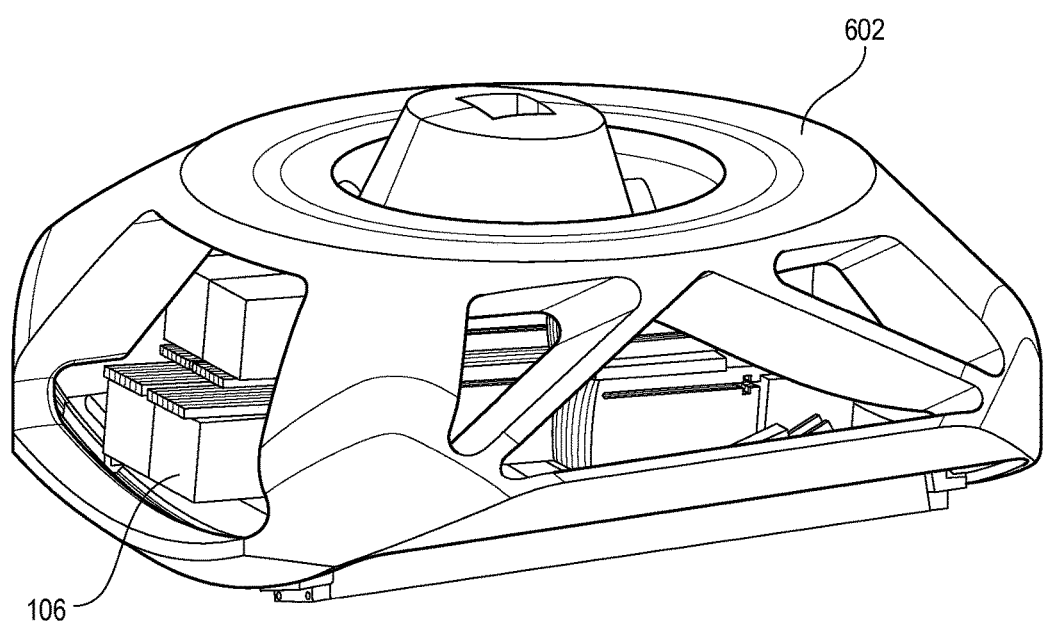
FIG. 6 illustrates an exemplary multileaf collimator mounted in a rotatable structure according to some embodiments of this disclosure.
Figure 7:
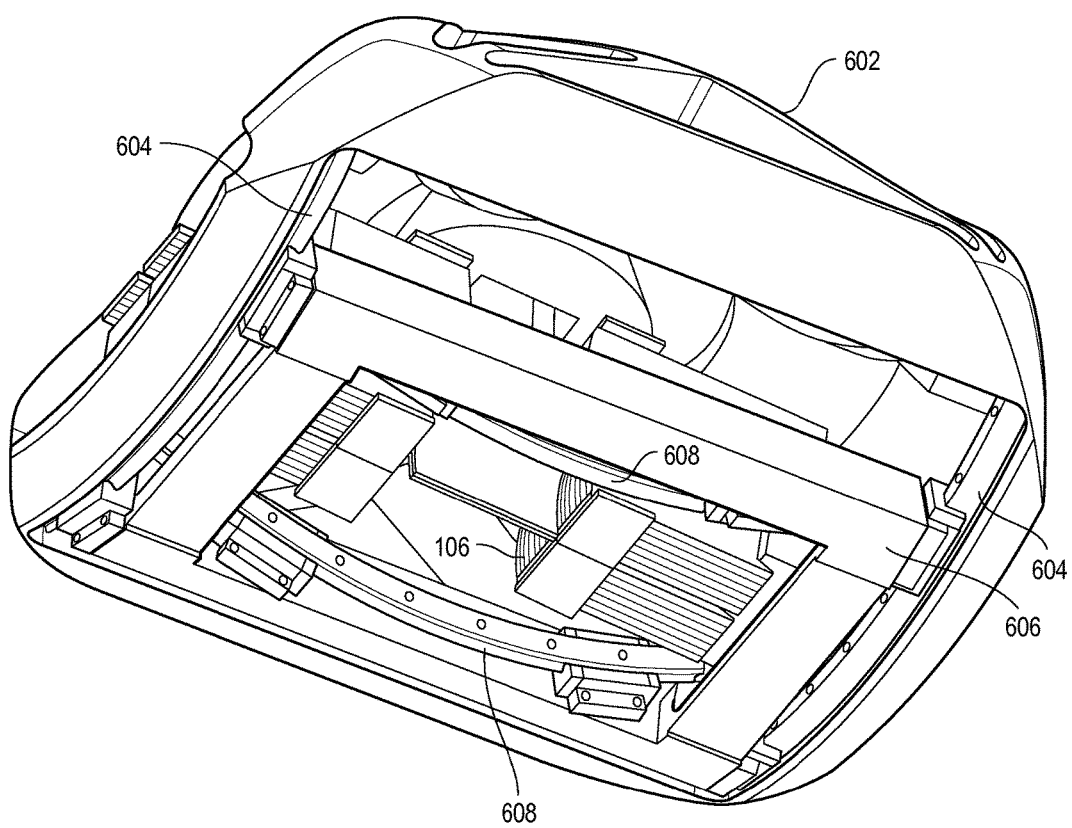
FIG. 7 is a perspective bottom view of the multileaf collimator mounted in the structure as shown in FIG. 6.

FIGS. 6-7 schematically show further exemplary rotating and pivoting mechanisms configured to pivot and rotate a multileaf collimator in a hierarchy different from that shown in FIGS. 1-5. As shown in FIGS. 6-7, the multileaf collimator 106 may be supported in a frame structure 602, which may be rotatably mounted to a gantry e.g. via a bearing assembly (not shown). Actuation of the bearing assembly may allow the frame structure 602, thus causing the multileaf collimator 106 mounted to the frame structure 602 to rotate about an axis through the source and the multileaf collimator. A first pair of segment rails 604 may couple a first stage 606 to frame structure 602 (FIG. 7). Actuation of the first pair of segment rails 604 may allow the first stage 606 to move, thus causing the multileaf collimator 106 to pivot about the source in a first degree of freedom. A second pair of segment rails 608 may couple the multileaf collimator 106 to the first stage 606. Actuation of the second pair of segment rails 608 may allow the multileaf collimator 106 to pivot about the source in a second degree of freedom.

Conventional multileaf collimators have been designed with the ability to provide a large maximal filed size in one instantaneous static exposure. For example, multileaf collimators with a maximal field size of 40×40 $cm^2$ in the patient plane with a radiation source 100 cm distant are available. However, such conventional MLCs generally can only provide about 15×40 $cm^2$ instantaneously available, fully independent field shaping area since the leaf reach in conventional MLCs is only 15 cm.

According to embodiments of this disclosure, a carriageless MLC can be constructed such that while they may provide a smaller maximal field size, they can nevertheless provide a larger fully independent field shaping area. The MLC leaf reach may be equal to the maximal aperture size so that each pair of leaf tip positions in a treatment planning strip would be fully independent of all of the other pairs of leaf tip positions in the other treatment planning strips. Therefore, despite a smaller instantaneous or maximal field size (e.g. 28×28 $cm^2$), embodiments of this disclosure make available both a larger fully independent shaping area for IMRT treatments and a larger fully independent shaping volume for VMAT treatments compared to conventional MLCs.

FIGS. 8A and 8B compare independent shaping of a two-dimensional (2D) treatment field using a conventional MLC and an MLC according to embodiments of this disclosure. FIG. 8A illustrates independent 2D field shaping using a conventional carriage MLC with a 15 cm leaf reach. The conventional carriage MLC may provide a maximal field size of 40×40 $cm^2$ when all of the leaves are fully retracted. To independently shape a treatment field having a generally straight shape as shown in the upper portion of FIG. 8A, each carriage would have to carry each bank of the leaves to a position (−15 cm, +15 cm) so that each leaf from either bank can reach to the neighborhood of the MLC centerline to form a generally straight aperture along the centerline of the MLC. Therefore, to shape a generally straight shape as shown in the upper portion of FIG. 8A, the fully independent field shaping area that can be provided by the conventional MLC would be about 1200 $cm^2$ (30×40 $cm^2$). To independently shape a 2D field having a generally sine shape as shown in the lower portion of FIG. 8A, each carriage would have to carry each bank of the leaves further to a position (−7.5 cm, +7.5 cm) so that some leaves from a bank can reach all the way to the area near the opposite carriage in order to form an aperture that constitutes a part of the generally sine shape. Therefore, to provide a generally sine field shape as shown in the lower portion of FIG. 8A, the fully independent 2D field shaping area that can be provided by the conventional MLC would be only about 600 $cm^2$ (15×40 $cm^2$).

FIG. 8B illustrates independent 2D shaping using an exemplary carriageless MLC of this disclosure with a 28 cm leaf reach. The exemplary carriageless MLC of this disclosure may provide a smaller maximal field size of 784 cm² (28×28 cm²) as compared to the conventional carriage MLC shown in FIG. 8A. However, within the smaller maximal field size, the MLC of this disclosure can provide fully independent shaping of 2D treatment fields of any shape, including generally straight and sine shapes, because each leaf from a bank can reach all the way to the opposing bank so that the tip of a leaf and the tip of a corresponding opposing leaf can form an aperture that may constitute a part of the field shape. Therefore, while the MLC of this disclosure may provide a smaller maximal field size, it can nevertheless provide a fully independent 2D field shaping in the entire treatment field, which is larger than the independent 2D shaping area provided by conventional MLCs (600 cm² for the sine shape).

FIGS. 9A, 9B, and 9C compare independent shaping of a three-dimensional (3D) treatment field using a conventional MLC and an MLC according to embodiments of this disclosure. FIG. 9A shows the independent shaping of a 3D treatment volume and a 2D treatment area using a carriageless MLC of this disclosure, which is constructed with a 28×28 cm² instantaneous field size and a 28 cm leaf overreach. At a collimator location such as at an angle of 45 degree with respect to the y-axis, the carriageless MLC of this disclosure can provide 28×28 cm² (784 cm²) fully independent 2D field shaping as shown in the upper portion of FIG. 9A and as described above in connection with FIG. 8B. Further, as shown in the lower portion of FIG. 9A, in a volumetric modulated arc therapy (VMAT) where the multileaf collimator may swivel together with the source in an arc such as in 180 or 360 degrees etc., the carriageless MLC of this disclosure can provide a fully independent 3D field shaping for a volume defined by a cylinder with a height of 28 cm and a top/bottom diameter of 28 cm.

FIGS. 9B and 9C show the independent 3D and 2D field shaping using a conventional MLC, which is constructed with a 40×40 cm² instantaneous field size and a 15 cm leaf overreach. FIG. 9B shows that at an MLC angle of 45 degree with respect to the y-axis, the conventional carriage MLC can provide 15×40 cm² (600 cm²) fully independent 2D field shaping as shown in the upper portion of FIG. 9B and as described above in connection with FIG. 8A. Further, as shown in the lower portion of FIG. 9B, in a volumetric modulated arc therapy (VMAT) where the MLC may swivel together with the source in an arc of 180 degrees, the conventional carriage MLC can provide an independent 3D field shaping for a volume defined by a cylinder with a height of 28 cm and a top/bottom diameter of 15 cm. In VMAT where the MLC may swivel together with the source in full 360 degrees, the conventional carriage MLC can only provide a fully independent 3D field shaping for a much smaller volume defined by a cylinder with a height of 15 cm and a top/bottom diameter of 15 cm. FIG. 9C shows that with an MLC angle at 20 degree and for a 180 degree VMAT, the conventional MLC can provide an independent 3D shaping for a volume defined by a cylinder with a height of 28 cm and a top/bottom diameter of 15 cm. For a full 360 degree VMAT, the conventional MLC can only provide a fully independent 3D shaping for a much smaller volume defined by a diamond as shown.

Figure 10A:
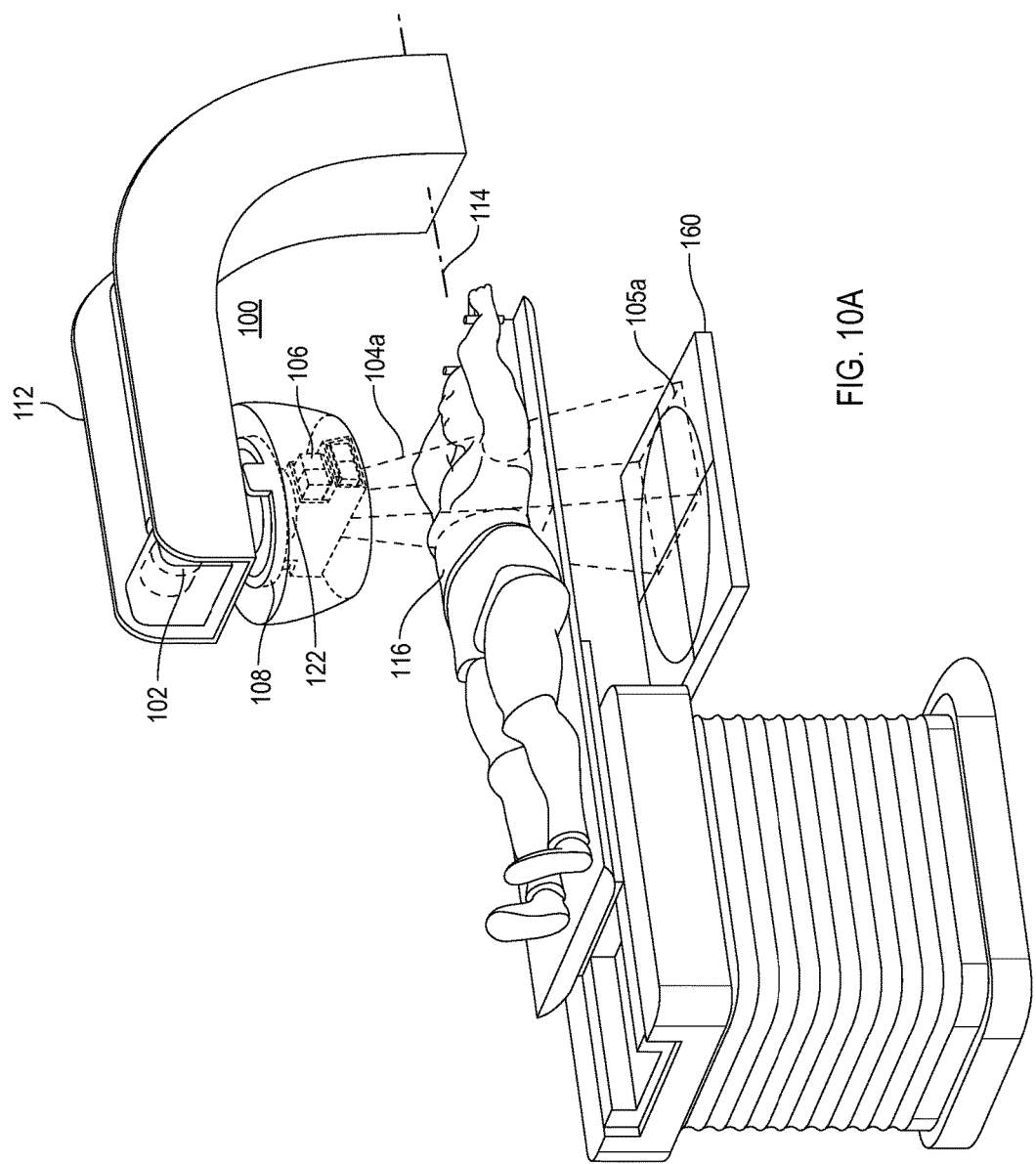

FIGS. 10A and 10B schematically show a method of field matching according to some embodiments of this disclosure. The apparatus 100 used in the method may include a source 102 operable to generate radiation beams, a multileaf collimator 106 operable to shape the radiation beams, and a pivoting mechanism 108 configured to pivot the multileaf collimator 106 about the source 102. The apparatus 100 may optionally include a rotating mechanism 122 configured to rotate the multileaf collimator 106 about an axis through the source and the collimator.

In the method, the radiation source 102 may first be positioned at a location relative to the patient 116. This can be achieved by swiveling the arm 112 supporting the source 102 about axis 114. While the source 102 remains at the location, the multileaf collimator 106 may be positioned or pivoted about the source 102 to a first position, as shown in FIG. 10A. A first beam or exposure 104a may be generated and delivered. The multileaf collimator 106 may shape the first beam 104a to define a first treatment field in a first area in the patient 116. For clarity of illustration and description, a reference plane 160, e.g. about 500 mm below the isoplane in the patient 116, is used in FIGS. 10A and 10B to show the field effects in the isocenter plane in the patient 116. For example, reference 105a in the reference plane 160 may virtually represent the first treatment area in the patient 116. Then the multileaf collimator 106 may be pivoted about the source 102 to a second position, as shown in FIG. 10B. A second beam or exposure 104b may be generated and delivered. The multileaf collimator 106 may shape the second beam 104b to define a second treatment field in a second area in the patient 116, as illustrated by reference 105b in the reference plane 160. The pivoting of the multileaf collimator 106 may be precisely controlled such that the first and second treatment fields 105a and 105b may adjoin seamlessly. A portion of the first treatment field 105a may overlap with a portion of the second treatment field 105b, and the first and second treatment fields 105a and 105b may be seamlessly combined using suitable algorithm. The combined first and second treatment fields may cover the entire treatment area as planned.

The source 102 may then be relocated to a different position relative to the patient 126 e.g. to a side or bottom or any other locations by swiveling the arm 112 about axis 114. Radiation may be delivered to the patient 116 from the additional locations of the source 102 using the steps described above in connection with FIGS. 10A and 10B.

Figure 11A:
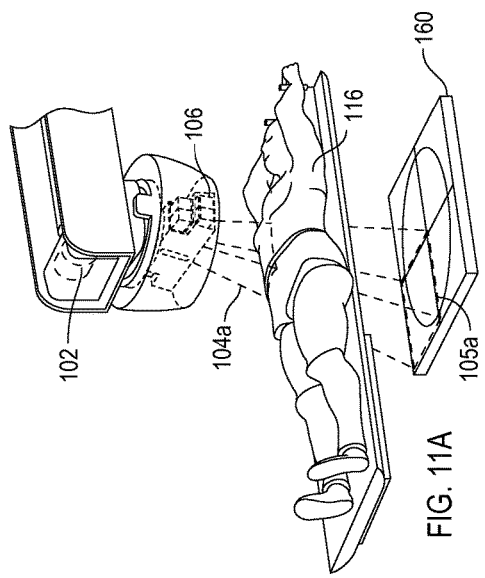
FIGS. 11A through 11D illustrate a radiation method according to some other embodiments of this disclosure.
Figure 11B:
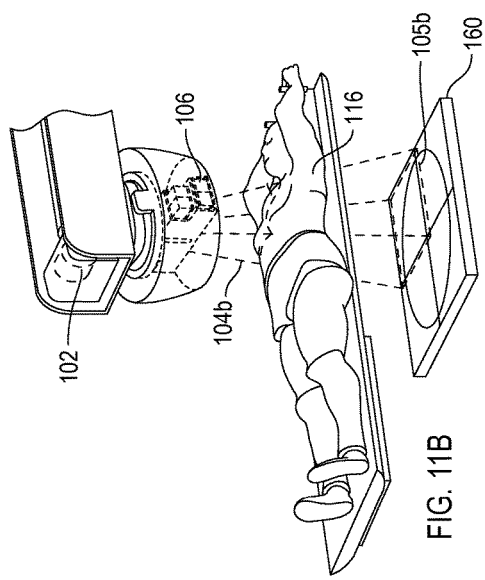
Figure 11C:
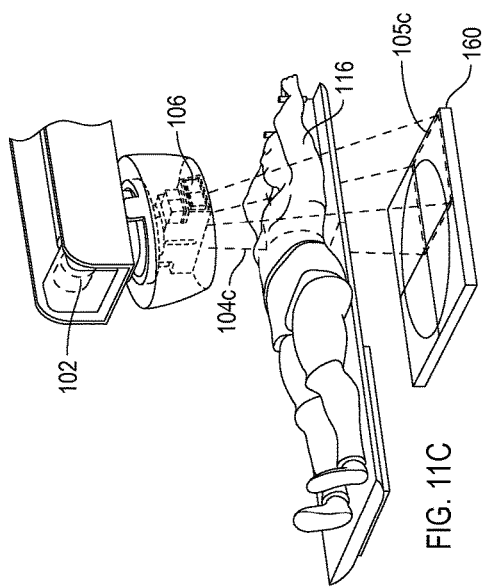
Figure 11D:
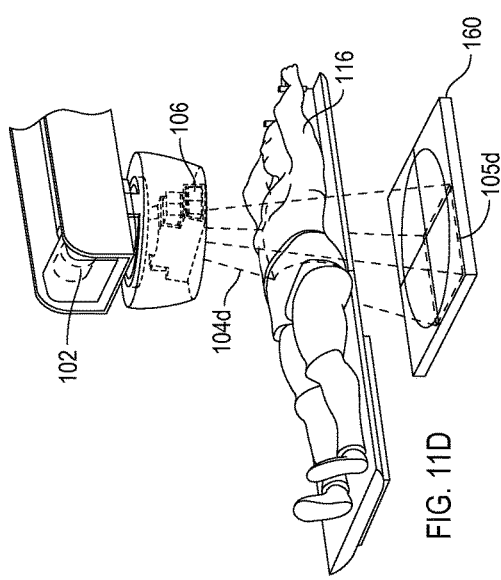

In some embodiments, the multileaf collimator 106 may be pivoted sequentially to a plurality of positions while the source 102 remains at the location. The multileaf collimator 106 may shape beams at the plurality of positions and provide a combined treatment field covering the entire treatment area in the patient. For example, while the source 102 remains at a location, the multileaf collimator 106 may be pivoted about the source 102 to a first position as shown in FIG. 11A. The source 102 may deliver a first beam 104a and the multileaf collimator 106 shape the first beam 104a, thereby defining a first treatment field 105a covering a first area in the patient 116. Then the multileaf collimator 106 may be pivoted about the source 102 to a second position as shown in FIG. 11B, and the source 102 may deliver a second beam 104b and the multileaf collimator 106 shape the second beam 104b, thereby defining a second treatment field 105b covering a second area in the patient 116. The multileaf collimator 106 may be further pivoted about the source 102 to a third position as shown in FIG. 11C, and the source 102 may deliver a third beam 104c and the multileaf collimator 106 shape the third beam 104c, thereby defining a third treatment field 105c covering a third area in the patient 116. Then the multileaf collimator 106 may be pivoted about the source 102 to a fourth position as shown in FIG. 11D, the source 102 may deliver a fourth beam 104d and the multileaf collimator 106 shape the fourth beam 104d, thereby defining a fourth treatment field 105d covering a fourth area in the patient 116. For clarity of illustration and description, a reference plane 160, e.g. about 500 mm below the iso-plane in the patient 116, is used in FIGS. 11A through 11D to show the field effects in the isocenter plane in the patient 116. For example, references 105a through 105d in the reference plane 160 may virtually represent the first through fourth treatment field in the patient 116. The pivoting of the multileaf collimator 106 about the source 102 may be precisely controlled such that the first, second, third, and fourth treatment fields may adjoin seamlessly. In some embodiments, a portion of a neighboring treatment field 105a-105d may slightly overlap each other, and the treatment fields may be seamlessly combined using a suitable algorithm. The pivoting the multileaf collimator 106 may be carried out in a clockwise or counterclockwise order and the first, second, third, and fourth treatment fields 105a-105d may adjoin in any other desirable ways.

In some embodiments, the source 102 may be relocated to different locations relative to the patient 116, and while the source remains at the new locations, the pivoting steps described above may be repeated to provide a treatment field while the source at the new locations. The source 102 may be rotated to a plurality of locations in an arc such as in 180 or 360 degrees in volumetric modulated arc therapy (VMAT).

Exemplary embodiments of a radiation apparatus and method are described. Those skilled in the art will appreciate that various modifications may be made within the spirit and scope of the disclosure. All these or other variations and modifications are contemplated by the inventors and within the scope of the disclosure.

What is claimed is:

1. A radiation apparatus, comprising:
   a source operable to generate a radiation beam;
   a multileaf collimator operable to shape the radiation beam;
   a pivoting mechanism configured to pivot the multileaf collimator about the source; and
   a rotating mechanism configured to rotate the multileaf collimator about an axis passing through the source and the multileaf collimator.

2. A radiation apparatus comprising:
   a source operable to generate a radiation beam;
   a multileaf collimator operable to shape the radiation beam; and
   a pivoting mechanism configured to pivot the multileaf collimator about the source;
   wherein the pivoting mechanism comprises a first pivoting mechanism configured to pivot the multileaf collimator about the source with a first degree of freedom and a second pivoting mechanism configured to pivot the multileaf collimator about the source with a second degree of freedom.

3. The radiation apparatus of claim 1 wherein the pivoting mechanism is supported by and rotatable with the rotating mechanism.

4. The radiation apparatus of claim 1 wherein the rotating mechanism is supported by and pivotable with the pivoting mechanism.

5. The radiation apparatus of claim 4 wherein the pivoting mechanism comprises a first pivoting mechanism configured to pivot the multileaf collimator about the source with a first degree of freedom and a second pivoting mechanism configured to pivot the multileaf collimator about the source with a second degree of freedom.

6. The radiation apparatus of claim 4 wherein the multileaf collimator is carriageless.

7. The radiation apparatus of claim 4 further comprising a unicarriage configured to translate the multileaf collimator in a linear direction, wherein the unicarriage is supported by and pivotable with the pivoting mechanism.

8. The radiation apparatus of claim 1 wherein the multileaf collimator is carriageless.

9. The radiation apparatus of claim 1 wherein the multileaf collimator comprises a plurality of pairs of leaves operable to define a maximal aperture when the leaves are fully retracted, the maximal aperture having a first dimension in a leaf travel direction, wherein each of the leaves of the multileaf collimator has a leaf travel length that is at least equal to the first dimension of the maximal aperture.

10. The radiation apparatus of claim 9 wherein the plurality of pairs of leaves are operable to define a maximal aperture in a shape of a square.

11. The radiation apparatus of claim 1 wherein the multileaf collimator comprises a plurality of leaves arranged in two or more levels with respect to the source.

12. The radiation apparatus of claim 1 wherein the multileaf collimator comprises a plurality of pairs of leaves arranged in a first section and a second section, wherein leaves of the first section are thinner than leaves of the second section.

13. The radiation apparatus of claim 1 wherein the pivoting mechanism comprises a universal joint configured to pivot the multileaf collimator about the source in all degrees of freedom.

14. A method of delivering radiation using a radiation apparatus, comprising:
   providing a radiation apparatus comprising a source operable to generate radiation beams, a multileaf collimator operable to shape the radiation beams, and a pivoting mechanism configured to pivot the multileaf collimator about the source, wherein the pivoting mechanism comprises a first pivoting mechanism configured to pivot the multileaf collimator about the source with a first degree of freedom and a second pivoting mechanism configured to pivot the multileaf collimator about the source with a second degree of freedom:
   positioning the source at a location relative to a subject, wherein while the source remains at the location:
   positioning the multileaf collimator relative to the source at a first position and delivering a first beam, wherein the multileaf collimator shapes the first beam to define a first treatment field in a first area in the subject; and
   pivoting the multileaf collimator about the source to a second position and delivering a second beam, wherein the multileaf collimator shapes the second beam to define a second treatment field in a second area in the subject;
   wherein the first and second treatment fields jointly provides a combined treatment field covering the first and second areas in the subject.

15. The method of claim 14 wherein the combined treatment field is substantially a two-dimensional (2D) field.

16. The method of claim 15 wherein the first and the second areas adjoin and are in a same plane.

17. The method of claim 14, wherein the multileaf collimator comprises a plurality of pairs of leaves which define a maximal aperture when the plurality of pairs of leaves are fully retracted, wherein:
   the maximal aperture provides a field covering the entire first or second area in the subject; and
   the maximal aperture has a first dimension in a leaf travel direction, wherein each of the plurality of the leaves has a leaf travel length at least substantially equal to the first dimension of the maximal aperture.

18. The method of claim 17 wherein the maximal aperture is in a shape of a square.

19. The method of claim 18 wherein the maximal aperture provides a field of about 28×28 cm$^2$ or greater covering the first or second area in the subject and the multileaf collimator provides a step resolution of about 5 mm or smaller in shaping the first and second treatment fields.

20. The method of claim 17, wherein while the source remains at the location, the method further comprising:

pivoting the multileaf collimator about the source to a third position and delivering a third beam, wherein the multileaf collimator shapes the third beam to provide a third treatment field in a third area in the subject; and pivoting the multileaf collimator about the source to a fourth position and delivering a fourth beam, wherein the multileaf collimator shapes the fourth beam to provide a fourth treatment field in a fourth area in the subject;

wherein the first, second, third, and fourth treatment fields jointly provide a combined treatment field covering the first, second, third, and fourth areas in the subject.

21. The method of claim 20 wherein the combined treatment field covering the first, second, third, and fourth areas is substantially a two-dimensional (2D) field.

22. The method of claim 21 wherein the steps of pivoting are carried out in a clockwise or counterclockwise order and the first, second, third, and fourth areas adjoin.

23. The method of claim 14 further comprising the step of positioning the source relative to the subject at an additional location relative to the subject, and while the source remains at the additional location, repeating the steps of positioning and pivoting of the multileaf collimator.

24. The method of claim 23, wherein the step of positioning the source at the additional location is carried out by swiveling the source and the multileaf collimator in an arc relative to the subject.

25. The method of claim 24, wherein the source and the multileaf collimator are swiveled in an arc subtending an angle ranging from about 30 to 360 degrees.

* * * * *